United States Patent
Impraim et al.

(10) Patent No.: US 6,228,578 B1
(45) Date of Patent: May 8, 2001

(54) NON-RADIOACTIVE HYBRIDIZATION ASSAY AND KIT

(75) Inventors: Chaka Impraim, N. Potomac; Sharon Challberg, Boyds; Attila Lörincz, Gaithersburg; Allison Cullen, Germantown, all of MD (US)

(73) Assignee: Digene Corporation, Gaithersburg, MD (US)

( * ) Notice: Subject to any disclaimer, the term of this patent is extended or adjusted under 35 U.S.C. 154(b) by 0 days.

(21) Appl. No.: 08/183,154

(22) Filed: Jan. 18, 1994

Related U.S. Application Data

(63) Continuation of application No. 07/792,585, filed on Nov. 14, 1991, now abandoned.

(51) Int. Cl.⁷ ............................. C12Q 1/68; C07H 21/04

(52) U.S. Cl. .................................. 435/6; 435/5; 435/7.1; 435/7.92; 536/25.4; 536/25.42

(58) Field of Search .......................... 435/6, 5, 7.1, 7.92; 536/25.42, 25.4; 935/77.78; 436/826, 501, 518

(56) References Cited

U.S. PATENT DOCUMENTS

| | | | |
|---|---|---|---|
| 4,563,417 | 1/1986 | Albarella et al. | 435/6 |
| 4,732,847 | 3/1988 | Stuart et al. | 435/6 |
| 4,743,535 | 5/1988 | Carrico | 435/6 |
| 4,833,084 | 5/1989 | Carrico | 435/240.27 |
| 4,965,188 | 10/1990 | Mullis et al. | 435/6 |
| 4,968,602 * | 11/1990 | Dattagupta | 435/6 |

FOREIGN PATENT DOCUMENTS

| | | |
|---|---|---|
| 0 135 159 | 3/1985 | (EP) . |
| 0 146 039 | 6/1985 | (EP) . |
| 0 209 702 | 1/1987 | (EP) . |
| 0 293 266 | 11/1988 | (EP) . |
| 0 339 686 | 11/1989 | (EP) . |
| WO 89/00577 | 1/1989 | (WO) . |
| 8900577 * | 1/1989 | (WO) . |

OTHER PUBLICATIONS

Yamane et al., "Rapid Detection of Specific Gene Sequences," *Nucleic Acids Research*, Symposium Series No. 20, pp. 91–92 (1988).

Barr et al., "Application of a Subtraction Hybridization Technique Involving Photoactivatable Biotin and Organic Extraction to Solution Hybridization Analysis of Genomic DNA", *Anal. Biochem.* 186:369–373 (1990).

Thompson, et al., "Current Concepts in Quantitative Molecular Hybridization", *Clin. Biochem.* 23:261–266 (1990).

Landry, et al., Nucleic Acid Hybridization in Viral Diagnosis:, *Clin. Biochem*, 23:267–277 (1990).

The Sigma Chemical Company Catalog, "Biochemical and Organic Compounds for Research and Diagnostic Clinical Reagents", pp. 261, 1149 (1986).

Thompson et al. Clin Biochem (Aug. 1990) 23: 261–266.*

Landry, M. Clin Biochem (Aug. 1990) 23: 267–277.*

Barr, F et al. Anal Biochem (May 1990) 186: 369–373.*

The Sigma Catalog, Biochemical and Organic Compound for Research and Diagnostic Clinical Reagents. 1986 p. 261 & 1149.*

(List continued on next page.)

Primary Examiner—Carla J. Myers
(74) Attorney, Agent, or Firm—Arnall Golden & Gregory, LLP

(57) ABSTRACT

A non-radioactive hybridization assay and kit for the detection of genetic defects, microbial infections or viral infections, such as human papillomavirus. A test sample is treated with a base and incubated with nucleic acid probes, diluted in a neutralizing buffer, specific for target nucleic acids. The hybrids are captured onto a solid phase coated with an anti-hybrid antibody, unhybridized probe is eliminated, and the bound hybrid detected.

17 Claims, 2 Drawing Sheets

OTHER PUBLICATIONS

Ansari et al., *J. Immunol. Methods* 84:117–124 (1985) "Elisa Solid Phase: Stability and Binding Characteristics".

Boguslawski et al., "Characterization of Monoclonal Antibody to DNA—RNA and Its Application to Immunodetection of Hybrids," *J. Immunol. Methods* 89:123–130 (1986).

Boshart, M. et al., "A New Type of Papillomavirus DNA, Its Presence in Genital Cancer Biopsies and in Cell Lines Derived From Cervical Cancer," *EMBO J.*, 3:1151–1157 (1984).

Coutlee, et al., *J. Clin. Microbiol.* 27:1002–1007 (1989) "Comparison of Colorimetric, Fluorescent, and Enzymatic Amplification Substrate Systems in an Enzyme Immunoassay for Detection of DNA–RNA Hybrids".

Du Clos, et al., "Monoclonal Antibody for DNA Measurement in Biological Fluids," *Journal of Immunological Methods*, 88:185–192 (1986).

Durst, M., et al., "A Papillomavirus DNA from a Cervical Carcinoma and Its Prevalence in Cancer Biopsy Samples from Different Geographic Regions," *Proc. Natl. Acad. Sci., USA*, 80:3812–3815 (1983).

Esser, P., Nunc Bulletin No. 6 (Nov. 1988) (Nunc. Roskilde, Denmark).

Fleminger, G., et al., *Appl. Biochem, Biotech*, 23:123–137 (1990) "Oriented Immobilization of Periodate–Oxidized Monoclonal Antibodies on Amino and Hydrazide Derivatives of Eupergit C".

Gissmann, L., "Papillomaviruses and Their Association with Cancer in Animals and in Man," *Cancer Surv.*, 3:161–181 (1984).

Grunstein et al., "Colony Hybridization: A Method for the Isolation of Cloned DNAs that Contain a Specific Gene," *Proc. Natl. Acad. Sci. USA* 72:3961–3965 (1975).

Haun, M. and Wasi, S., *Anal, Biochem*, 191:337–342 (1990 "Biotinylated Antibodies Bound to Streptavidin Beads: A Versatile Solid Matrix for Immunoassays".

Hoofnagle et al., *J. Hepatol*, 11:S100 (1990) "a–Interferon therapy of chronic hepatitis B. Current status and recommendations".

Ishikawa et al., *J. Immunoassay* 4:209–237 (1983) "Enzyme–Labeling of Antibodies and Their Fragments for Enzyme Immunoassay and Immunohistochemical Staining".

Kitawaga, Y, and Stollar, B.D., *Mol. Immunology* 19:413–420 (1982) "Comparison of Poly(A)–Poly(dt) and Poly(I)–Poly(dC) As Immunogents for the Induction of Antibodies to RNA–DNA Hybrids".

Lorincz A.T. et al., *J. Virol*, 58:225 (1986) "Cloning and Characterization of the DNA of a New Human Papillomavirus from a Woman with Dysplasia of the Uterine Cervix".

Maniatis, T., et al., Molecular Cloning: A Laboratory Manual, Cold Spring Harbor Laboratory, Cold Spring Harbor, NY (1989).

Miller, et al., "Detection of Bacteria by Hybridization of rRNA with DNA–Latex and Immunodetection of Hybrids," *Journal of Clinical Microbiology*, vol. 26, No. 7, pp. 1271–1276 (Jul. 1988).

Means, G. and Feeney, R., *Bioconi, Chem*, 1: 2–12 (1990) "Chemical Modifications of Proteins: History and Applications".

Nunc Bulletin No. 9, pp. 1–4 (Jun. 1991) (Nunc, Roskilde, Denmark).

Pfister, H., *Rev. Physiol, Biochem, Pharmacol.*, 99:111–181 (1984) "Biology and Biochemistry of Papillomaviruses".

Southern, "Detection of Specific Sequences Among DNA Fragments Separated by Gel Electrophoresis," *J. Mol. Biol.* 98:503–517 (1975).

Stuart et al., "Location of the 18/28S Ribosomal RNA Genes in Two Hawaiian Drosophila Species by Monoclonal Immunological Identification of RNA–DNA Hybrids in situ," *Proc. Natl. Acad. Sci., USA* 78:3751–3754 (1981).

Yehle, et al., "A Solution Hybridization Assay for Ribosomal RNA from Bacteria Using Biotinvlated DNA probes and Enzyme–Labeled Antibody to DNA:RNA," *Molecular and Cellular Probes*, 1:177–193 (1987).

Esser, P., Nunc Bulletin No. 8, pp. 1–5 (Dec. 1990).

\* cited by examiner

NICK AND DENATURE SPECIMEN DNA BY BASE HYDROLYSIS.

HYBRIDIZE SAMPLE TO HPV SPECIFIC RNA PROBE.

CAPTURE HYBRIDS ON TUBE COATED WITH POLYCLONAL ANTIBODY TO RNA/DNA HYBRID.

DETECT WITH ALKALINE PHOSPHATASE CONJUGATE OF MONOCLONAL ANTIBODY TO RNA/DNA HYBRID.

SIGNAL IS GENERATED WITH LUMI-PHOS™ 530, CHEMILUMINESCENT SUBSTRATE FOR ALKALINE PHOSPHATASE.

NON-RADIOACTIVE HYBRIDIZATION ASSAY AND KIT

This is a continuation of application Ser. No. 07/792,585 filed on Nov. 14, 1991 now abandoned.

This relates to the field of hybridization probe assays in general and more particularly relates to a non-radioactive hybridization immunoassay.

BACKGROUND OF THE INVENTION

Hybridization Probes

The RNA or DNA for many microorganisms and viruses have been isolated and sequenced. Nucleic acid probes are currently available to identify a large number of infections. Nucleic acid probes are detectable nucleic acid sequences that hybridize to complementary RNA or DNA sequences in a test sample. Detection of the probe indicates the presence of a particular nucleic acid sequence in the test sample for which the probe is specific. In addition to aiding scientific research, DNA or RNA probes can be used to detect the presence of viruses and microorganisms such as bacteria, yeast and protozoa as well as genetic mutations linked to specific disorders in patient samples. Grunstein et al., *Proc. Natl. Acad. Sci. USA* 72:3961 (1975) and Southern, *J. Mol. Biol.* 98:503 (1975) describe hybridization techniques using radiolabelled nucleic acid probes. Nucleic acid hybridization probes have the advantages of high sensitivity and specificity over other detection methods and do not require a viable organism. Hybridization probes are often labelled with a radioactive substance that can be easily detected. A radioactive hybridization assay for HPV is currently available in the form of the ViraType™ or ViraPap™ kit by Digene Diagnostics (Silver Spring, Md.).

The existing hybridization techniques that utilize radioisotopes to label probes introduce additional expenses for disposal of radioactive waste products and monitoring of personnel and the workplace for contamination. In addition, the short half-life of radioactive compounds such as $^{32}P$ requires that radioactive probes be produced frequently. Radioactive nucleic acid hybridization is therefore discouraged in commercial areas such as clinical diagnosis.

Probes have been indirectly labelled in an attempt to avoid the problems associated with direct radioactive labelling. The most common method of indirect labelling is to attach biotin, a small vitamin, to the nucleic acid using a chemical or enzymatic technique. Following hybridization, the biotin is detected by reaction with avidin, an egg white protein which has been labelled with an enzyme or fluorochrome. Bound enzyme can be detected by reaction with color-producing substrates and the fluorochrome can be seen when reacted with incident light of appropriate wavelength. Indirect labelling of hybridization probes with biotin or other haptens often increases the "hydrophobicity" of the probe. The probe tends to interact non-specifically with materials other than the complementary nucleic acid target, leading to high background. High background reduces sensitivity and increases the likelihood of a false-positive result. Indirect labelling is also less sensitive than direct labelling because the labelling density is limited; only a small fraction of the bases are labelled giving a limiting number of sites for signal generation. An increase in the labelling density of a probe leads to increased non-specific binding, higher background, and ultimately, failure of the probe to hybridize with its target due to the interference of the hapten with base pairing. Indirectly labelled probes are therefore not well suited to clinical diagnosis.

Hybridization has been detected with the use of an intercalating agent such as acridine orange or ethidium bromide as described in U.S. Pat. No. 4,563,417 to Albarella et al. The intercalating agent becomes inserted between hybridized base pairs of probe and sample nucleic acids and causes the tertiary structure of the helix to unwind. An antibody specific for the newly formed antigenic determinant created by the intercalating agent and the unwound helix is detected by conventional means. This method lacks selectivity for the target hybrids because intercalating agents fail to recognize specific sequences. Furthermore, the antibodies recognize only the intercalating agent/nucleic acid complex, but do not detect a specific sequence. Therefore, additional selection or purification steps are required to prevent non-specific signal, making this approach poorly suited for clinical diagnosis.

Hybridization can also be detected with the aid of an antibody specific for a labelled probe as described in U.S. Pat. No. 4,743,535 to Carrico. The probe is labelled with a detectable substance such as flavin adenine dinucleotide (FAD) or a fluorescent agent. An antibody specific for the labelled probe, after it has hybridized to the sample nucleic acid, is detected by a biochemical reaction. This method of detection also creates non-specific binding and the likelihood of false-positive results and is not well suited for clinical screening.

Monoclonal antibodies to DNA-RNA hybrids are now available. U.S. Pat. No. 4,732,847 to Stuart et al. and the publication of Stuart et al., *Proc. Natl. Acad. Sci., USA* 78:3751 (1981) describe a method of hybridization detection involving a monoclonal antibody specific for a poly(A)-poly(dT) duplex. A monoclonal antibody specific for DNA-RNA hybrids, secreted by hybridoma HB 8730, is disclosed in U.S. Pat. No. 4,833,084 to Carrico et al. The isolation of anti-DNA-RNA hybridomas has improved the development of assays for genetic mutations linked to specific defects and the detection of bacterial and viral infections. However, assays utilizing these anti-hybrid monoclonal antibodies often suffer from a high level of non-specific binding causing false positive results. Boguslawski et al., *J. Immunol. Methods* 89:123–130 (1986) developed a hybridization assay using anti-hybrid coated polystyrene beads isolated on filter paper in an attempt to reduce non-specific binding and avoid complicated washing procedures.

Infections by Microorganisms and Viruses

Neoplastic transformation of a normal cell to a cancer cell is known to be caused by chemical, physical and viral agents. Several varieties of oncogenic DNA and RNA viruses including papillomavirus and herpes viruses, such as Epstein-Barr virus, are known to induce tumor formation in humans. Prevention of these cancers, such as cervical cancer, lies in early detection and treatment of pre-cancerous disease.

Human papillomavirus, or HPV, has been recognized as the cause of various epithelial lesions such as warts, condylomas and dysplasias as described by Gissmann, L., *Cancer Surv.*, 3:161 (1984); Pfister, H., *Biochem. Pharmacol.*, 99:111 (1983); Durst, M. et al., *Proc. Natl. Acad. Sci., USA*, 80:3812 (1983) and Boshart, M. et al., *EMBO J.*, 3:1151 (1984). Dysplasias of the cervix are believed to be early events in the progression to cervical cancer; the progression proceeding from mild dysplasia (cervical intraepithelial neoplasia I or CIN I) to moderate dysplasia (CIN II) to severe dysplasia, to carcinoma in situ (collectively referred to as CIN III) to invasive cancer. Early detection and characterization of HPV is important for preventing progression of the disease to carcinoma.

Numerous types of HPV have been identified, and not all HPV infections are oncogenic. For example, HPV 6 and HPV 11 are associated with benign lesions, whereas HPV 16 and HPV 18 are detected in cervical and other anogenital cancers and their precursor lesions. The determination of the type of HPV infection is therefore essential for proper diagnosis, risk assessment of cancer development, and treatment.

Hepatitis B virus (HBV), formerly termed serum hepatitis, is an occupational disease of health personnel. HBV infection in humans can cause severe jaundice, liver degeneration and death. HBV enters predominantly by the parenteral route, has a characteristic incubation period of 60 to 160 days, and may persist in the blood for years in chronic carriers. HBV is detected by immunologic techniques such as immune electron microscopy, complement-fixation, immune adherence, enzyme-linked immunosorbent assay (ELISA) or radioimmunoassay (RIA). All blood for transfusion must be screened for HBV to prevent transmission of the virus to blood recipients. Early detection of HBV in infected patients is also important because exposure to blood or objects potentially contaminated with blood or even body excretions may cause infection.

Conventional HBV DNA assays test for the presence of hepatitis B virus genomic DNA in human serum using a full genomic (3.2 Kb) RNA probe. For HBV DNA testing a quantitative assay would be particularly advantageous because the level of HBV DNA in serum correlates with severity of liver disease. A quantitative HBV DNA test would be useful for monitoring chronic carriers of HBV undergoing antiviral therapy as detailed by Hoofnagle et al., *J. Hepatol.* 11:S100 (1990).

Chlamydiaceae (Chlamydia) is a family of obligate intracellular bacterial parasites. The organisms are spherical and form intracytoplasmic microcolonies up to 12 microns in diameter. Chlamydia infect a number of different birds and mammals including humans. Human diseases caused by Chlamydia include trachoma, inclusion conjunctivitis, various urogenital tract infections, infantile pneumonia, lymphogranuloma venereum, and psittacosis. Two species are recognized, *C. psittaci* and *C. trachomatis*, the latter being inhibited by sulfonamides. Most of the human Chlamydia infections are caused by various strains of *C. trachomatis*. *C. psittaci* is found mainly in birds and mammals, but can cause some disease in humans.

Diagnosis of Chlamydia is accomplished by either the complement-fixation test or the microimmunofluorescence technique. Neither test can be used to detect all human chlamydial infections. The complement-fixation test measures antibody to the antigen lipopolysaccharide (LPS). It is of little use in diagnosing trachoma and genital infections. Many patients without a chlamydial infection are seropositive by the complement fixation test, reducing the sensitivity of this test. The microimmunofluorescence test detects the presence of specific antibodies to strains of *C. trachomatis*. The level of seropositivity for uninfected patients is also high, reducing the sensitivity of this test as well. Direct culture methods have also been used to detect chlamydial infections but these methods require the presence of viable organisms. Enzyme immunoassays have also been used to detect chlamydia-specific antigens, but the performance of these assays is inferior to the above-mentioned culture methods.

In summary, there is a need for a hybridization assay for clinical diagnosis and quantitative analysis of microbial and viral infections, especially HPV, HBV and Chlamydia, and genetic mutational defects, that is economically feasible for screening large numbers of samples with great sensitivity and minimal non-specific binding.

It is therefore an object of the present invention to provide a cost-effective, sensitive, non-radioactive hybridization assay for the detection of nucleic acids in a sample.

It is a further object of the present invention to provide a cost-effective, sensitive, non-radioactive hybridization assay for the quantitation of nucleic acids in a sample.

It is a further object of the present invention to provide a hybridization assay in which sample preparation is simple and rapid.

It is a further object of the present invention to provide a hybridization assay in which sample preparation does not involve extractions, precipitations, centrifugations or other time-consuming purification methods.

It is a further object of the present invention to provide a non-radioactive hybridization assay having minimal false positives.

It is a further object of the present invention to provide an accurately quantitative test for monitoring the level of microbial and viral infection.

It is a further object of the present invention to provide a kit that can be used to screen large numbers of samples for microbial and viral infections.

SUMMARY OF THE INVENTION

A non-radioactive hybridization assay and kit are provided for screening samples for viral and other specific nucleic acid sequences. A hybridization buffer is also provided.

A test sample is collected with a chemically inert device and is treated with a base. The treated sample is incubated with nucleic acid probes, diluted in a neutralizing buffer, that are specific for target nucleic acid sequence, such as oncogenic and non-oncogenic HPV DNA sequences, HBV DNA sequences or Chlamydia DNA sequences, for a sufficient amount of time to allow hybridization of the sample nucleic acid sequence to the probes. The hybrids are then bound to anti-hybrid antibodies immobilized on a solid phase. Non-hybridized probe is removed, preferably by incubating the captured hybrids with an enzyme, such as RNAase, that degrades non-hybridized probe. Hybridization is detected by conventional means such as a direct labelled anti-hybrid antibody, a labelled antibody specific for an unlabelled anti-hybrid antibody, a direct labelled probe or a modified probe for which a labelled antibody is specific.

DETAILED DESCRIPTION OF THE INVENTION

Figure 1:
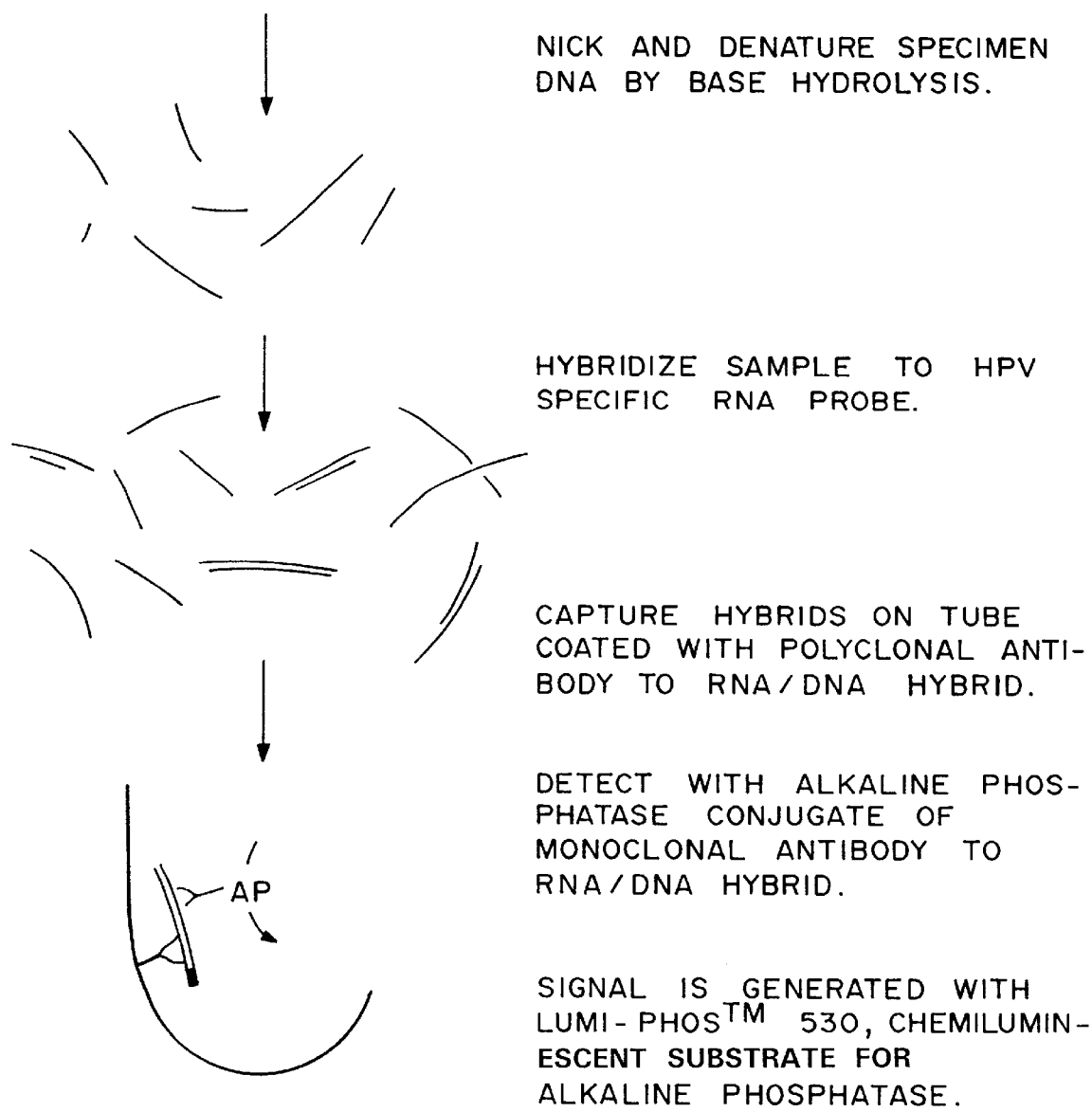
FIG. 1 is a schematic representation of the hybridization assay of the present invention for detection of HPV DNA.

A non-radioactive hybridization assay and kit are provided for the detection of target nucleic acid sequences specific for genetic disorders, microorganisms and viruses such as the DNA of Chlamydia, human papilloma virus (HPV), and hepatitis B virus. As shown in FIG. 1, the assay is performed generally as follows.

A sample such as blood or an exfoliated cervical cell specimen is collected and subjected to alkaline pH to denature and, if necessary, nick the nucleic acids in the sample. The treated, or hydrolyzed, target nucleic acids are hybridized to a probe or group of probes diluted in a neutralizing buffer. Most preferably, the target nucleic acids are DNA and the probe is a complementary RNA sequence.

An anti-hybrid antibody, either polyclonal or monoclonal, is immobilized on a solid phase such as a test tube or polystyrene bead. It will be understood by those skilled in the art that the immobilized antibody can be bound directly to the solid phase or indirectly by use of a primary binding antibody or protein, such as streptavidin or protein G, that is bound to the solid phase and which subsequently binds the anti-hybrid antibody, a derivatized anti-hybrid antibody, a functional fragment of the anti hybrid antibody, or a derivatized functional fragment of the anti-hybrid antibody. Any solid phase such as plastic or glass microparticles, beads, dip-sticks, test tubes or microtiter plates can be used.

The hybridized sample is placed in the antibody-coated tube for a sufficient amount of time to allow binding or capture of the hybrid by the anti-hybrid antibody. An enzyme that digests single-stranded RNA or RNA—RNA hybrids, such as an RNAase is then added to the sample to eliminate any non-hybridized probe. Most preferably, the RNAase and a hybrid detection means, described below are combined as a single reagent. Alternatively, non-hybridized probe can be removed by washing the sample.

Hybridization is then detected by conventional means well known in the art such as with a direct labelled polyclonal or monoclonal antibody specific for the hybrid, a labelled antibody specific for an unlabelled anti-hybrid antibody, or the RNA probe or probes can be directly labelled, or modified and detected with a labelled antibody specific for the modified probe. Most preferably, the label is an enzyme, a fluorescent molecule or a biotin-avidin conjugate and is non-radioactive. The label can then be detected by conventional means well known in the art such as a calorimeter, a luminometer or a fluorescence detector.

The non-radioactive hybridization assay and kit is described in more detail below.

Sample Collection and Hydrolysis

An exfoliated cell sample is collected with a chemically inert collection device such as a dacron tipped swab as shown in FIG. 1. The sample and collection device are stored in a transport medium that preserves nucleic acids and inhibits nucleases such as a chaotropic salt solution, a detergent solution such as sodium dodecyl sulfate (SDS), preferably 0.5% SDS, or a chelating agent solution such as ethylenediaminetetraacetic acid (EDTA), preferably 100 mM, to prevent degradation prior to analysis. Most preferably, the sample and collection device are stored in the chaotropic salt solution provided as the sample transport medium in the ViraPap™ human papilloma virus test kit available from Digene Diagnostics, Inc. (Silver Spring, Md.). Alternatively, the sample can be collected and stored in the base hydrolysis solution described below.

If the nucleic acids to be detected are present in blood, such as HBV DNA, a blood sample is collected with a syringe, and serum is separated by conventional means. Preferably, serum is incubated for approximately 20 minutes at approximately 65° C. with a protease, such as proteinase K, available from Sigma (St. Louis, Mo.), prior to base treatment as described below.

The sample is treated with a base, or hydrolyzed, to render the target nucleic acid accessible to hybridization. Nucleic acids are denatured and, if necessary, nicked by incubating the sample and collection device, if present, in 0.1 to 2.0 M base at 20 to 100° C. for 5 to 120 minutes. Preferably, treatment is achieved with 0.2 to 0.8 M NaOH, or a similar base such as KOH, at 60–70° C. for 30 to 60 minutes. Most preferably, the sample and swab are incubated in 0.415 M NaOH for 65° C. for 45 minutes. Approximately one volume of sample is treated with one-half volume of base, also referred to herein as the hydrolysis reagent. The pH will be approximately 13. This basic pH will both nick and denature a majority of the nucleic acid in the specimen. In addition, base treatment disrupts interactions between peptides and nucleic acids to improve accessibility of the target nucleic acid, degrade protein, and liquify mucous. Base treatment of protein and mucous effectively homogenizes the specimen to ensure reproducibility of analysis results for a given sample. Base treatment also reduces the viscosity of the sample to increase kinetics, homogenize the sample, and reduce background by destroying any existing DNA-RNA or RNA—RNA hybrids in the sample. It is believed that base treatment also inactivates enzymes such as RNAases present in the sample that could potentially degrade RNA probes used in the assay.

Hybridization

Non-radioactive RNA probes are synthesized or isolated in accordance with methods well known in the art as described by Maniatis, T., et al., *Molecular Cloning: A Laboratory Manual*, Cold Spring Harbor Laboratory, Cold Spring Harbor, N.Y. (1989). For example, HPV probes can be synthesized from linearized plasmid template using phage T7 RNA polymerase obtained from Bethesda Research Labs (Gaithersburg, Md.).

In the preferred embodiment, the probes are HPV RNA, most preferably a mixture of HPV 6 and HPV 11, which are associated with benign lesions, or a mixture of HPV 16, HPV 18, HPV 31, HPV 33, and HPV 35, which are associated with an increased risk of cervical cancer. Probes are preferably single-stranded RNA of approximately 20–10,000 bases in length. Mixtures of probes for use in screening assays include mixtures of HPV types 6, 11, 42, 43, and 44 RNA probes; HPV types 16, 18, 31, 33, and 35; and HPV types 6, 11, 16, 18, 31, 33, and 35 RNA. Probes are prepared by enzymatic or chemical in vitro synthesis. Probes can also be prepared so that they are linked to detectable labels, such as an enzyme, or to a hapten such as biotin that can then be detected with an anti-hapten antibody.

Preferably, the probe is diluted in a probe diluent that also acts as a neutralizing hybridization buffer. The diluent is used to dissolve and dilute the probe and also helps restore the sample to neutral pH, between approximately pH 6 and pH 9, to provide a more favorable environment for hybridization. Sufficient volume of probe diluent, preferably one-half volume, is used to neutralize one and one-half volume of base-treated sample. Preferably, the probe diluent is a 2-[bis(2-Hydroxyethyl) amino] ethane sulfonic acid (BES, Sigma, St. Louis, Mo.)/sodium acetate buffer. Most preferably, the probe diluent is a mixture of 2 M BES, 1 M sodium acetate, 0.05% of the antimicrobial agent $NaN_3$, 5 mM of the metal chelating agent EDTA, 0.4% of the detergent Tween™-20 and 20% of the hybridization accelerator dextran sulfate. The pH of the probe diluent is between approximately 5 to 5.5. The concentration of each probe in the probe diluent is from 1 to 500 ng/ml. Preferably, the concentration of probe is 20 to 200 ng/ml. Most preferably, the concentration of each probe is approximately 75 ng/ml.

After treatment with base, an aliquot is removed from the sample tube and combined with a sufficient amount of probe, dissolved in the above-described probe diluent, to allow hybridization. Preferably, 150 µl of base-treated sample are neutralized with 50 µl probe diluent. The probes and sample nucleic acids are incubated for approximately 5 to 120 minutes at 20 to 80° C. to allow hybridization. Preferably, RNA probes and sample DNA are incubated for 30 to 60 minutes at 50 to 80° C. Most preferably, the RNA probes and DNA in the sample are incubated for 60 minutes at 65° C.

Preparation of Anti-hybrid Antibodies for Capture

Any anti-hybrid antibodies may be used to capture the hybrid onto the solid phase that are specific for a double-stranded RNA/DNA. In a preferred embodiment of the present assay, a polyclonal anti-RNA/DNA hybrid antibody is derived from goats immunized with an RNA/DNA hybrid. Hybrid-specific antibody is purified from the goat serum by affinity purification against RNA/DNA hybrid immobilized on a solid support. Monoclonal antibody prepared using standard techniques can be used in place of the polyclonal antibodies.

The preferred antibody for capture of RNA/DNA hybrids is prepared by the method of Kitagawa, Y. and Stollar, B. D., Mol. Immunology 19:413–420 (1982) or according to the method set forth in U.S. Pat. No. 4,732,847, issued Mar. 22, 1988 to Stuart et al. While any vertebrate may be used for the preparation of anti-RNA/DNA hybrid monoclonal antibodies, goats or rabbits are preferred. Preferably, a goat or rabbit is immunized with a synthetic poly(A)-poly(dT) hybrid by injecting the hybrid into the animal in accordance with conventional injection procedures. Polyclonal antibodies may be collected and purified from the blood of the animal with antibodies specific for the species of the immunized animal in accordance with well-known antibody isolation techniques. For the production of monoclonal antibodies, the spleen is removed from the animal after a sufficient amount of time, and splenocytes are fused with the appropriate myeloma cells to produce hybridomas. Hybridomas are then screened for the ability to secrete the anti-hybrid antibody. Selected hybridomas may then be used for injection into the peritoneal cavity of a second animal for production of ascites fluid, which may be extracted and used as an enriched source of the desired monoclonal antibodies incorporated herein by reference.

It will be understood by those skilled in the art that either polyclonal or monoclonal anti-hybrid antibodies can be immobilized on the solid phase in the present assay as described below.

Immobilization of Anti-hybrid Antibody

The anti-hybrid antibody is immobilized onto a solid phase such as a test tube surface. It will be understood by those skilled in the art that a solid phase includes polystyrene, polyethylene, polypropylene, polycarbonate or any solid plastic material in the shape of test tubes, beads, microparticles, dip-sticks or the like. A solid phase also includes glass beads, glass test tubes and any other appropriate shape made of glass. A functionalized solid phase such as plastic or glass that has been modified so that the surface contains carboxyl, amino, hydrazide or aldehyde groups can also be used. Immobilization of the antibody can be direct or indirect. Preferably, test tubes are directly coated with anti-hybrid antibody in accordance with methods known to those skilled in the art or briefly described below. The antibody can also be biotinylated and subsequently immobilized on streptavidin coated tubes, or modified by other means to covalently bind to the solid phase. Solubilized biotinylated antibody can be immobilized on the streptavidin coated tubes before capture of the hybridized samples as described below or in conjunction with the addition of the hybridized samples to simultaneously immobilize the biotinylated antibody and capture the hybrids.

Most preferably, the antibody is attached to the solid phase in accordance with the method of Fleminger, G., et al., Appl. Biochem. Biotech. 23:123–137 (1990), by oxidizing the carbohydrate portion of the antibody with periodate to yield reactive aldehyde groups. The aldehyde groups are then reacted with a hydrazide-modified solid phase such as MicroBind-HZ™ microtiter plates available from Dynatech Laboratories (Chantilly, Va.). Passive coating of the antibody according to the well known method of Esser, P., Nunc Bulletin No. 6 (November 1988) (Nunc, Roskilde, Denmark) is also acceptable.

Alternatively, Ventrex Star™ tubes (Ventrex Laboratories Inc., Portland, Me.) are coated with streptavidin by the method of Haun, M. and Wasi, S., Anal. Biochem. 191:337–342 (1990). After binding of streptavidin the biotinylated goat polyclonal antibody described above, or otherwise produced by methods known to those skilled in the art, is bound to the immobilized streptavidin. Following antibody binding, tubes can be post-coated with a detergent such as Tween™-20 and sucrose to block unbound sites on the tube and stabilize the bound proteins as described by Esser, P., Nunc Bulletin No. 8, pp. 1–5 (December 1990) and Nunc Bulletin No. 9, pp. 1–4 (June 1991) (Nunc, Roskilde, Denmark) and Ansari, et al., J. Immunol. Methods 84:117–124 (1985). Preferably, each tube is coated with between 10 ng and 100 µg biotinylated antibody. Most preferably each tube is coated with approximately 250 ng of biotinylated antibody.

As discussed above, the solid phase can be coated with functional antibody fragments or derivatized functional fragments of the anti-hybrid antibody.

Capture

Hybridized samples are incubated in the anti-hybrid coated tubes for a sufficient amount of time to allow capture of the hybrids by the immobilized antibodies. The hybrids are bound to the immobilized antibodies by incubation for 5 minutes to 24 hours at 15 to 65° C. on a platform shaker with a shaking speed of 0 to 1500 rpm. Preferably, the incubation time is 30 to 120 minutes at 20 to 40° C., with shaking at 300 to 1200 rpm. Most preferably, capture occurs with incubation at one hour at room temperature with vigorous shaking on a rotary platform shaker with a rotary shaking speed between approximately 300 and 1000 rpm. It will be understood by those skilled in the art that the incubation time, temperature, and shaking can be varied to achieve alternative capture kinetics as desired.

Conjugation of Anti-hybrid Antibody

An antibody, specific for the RNA/DNA hybrid is conjugated to a label for detection of captured hybridized probe by well known conjugation methods. Preferably, an antibody, such as the mouse monoclonal antibody deposited with the American Type Culture Collection as ATCC Accession number HB-8730, is conjugated to a detectable label such as alkaline phosphatase. It will be understood by those skilled in the art that any detectable label such as an enzyme, a fluorescent molecule or a biotin-avidin conjugate can be used.

The antibody conjugate is produced by well known means such as direct reduction of the monoclonal antibody with dithiothreitol, (DTT, Sigma Chemical Company, St. Louis, Mo.) to yield monovalent antibody fragments. The reduced antibody is then directly conjugated to maleimated alkaline phosphatase by the methods of Ishikawa et al., *J. Immunoassay* 4:209–237 (1983) and Means, G. and Feeney, R., *Bioconj. Chem.* 1: 2–12 (1990) and the resulting conjugate is purified by HPLC.

Alternatively, captured hybrid can be detected indirectly using an unlabelled anti-hybrid antibody for which a labelled antibody is specific. For example, the anti-hybrid antibody can be a mouse immunoglobulin that is detected by a labelled goat anti-mouse antibody.

In addition, captured hybrid can be detected by conjugating the RNA probe used for hybridization to a label, such as an enzyme, or to a hapten, such as biotin that is then detected with a labelled anti-hapten antibody.

Excess Probe Digestion and Hybrid Detection

After capture, any excess sample is removed from the capture tube, a solution preferably containing both a single-stranded RNA digestion enzyme such as RNAase at a concentration between 0.01 and 1 mg/ml and the above described conjugated anti-hybrid molecule is added to the tube, and the tube is incubated for approximately 5 minutes to 24 hours at temperature between 4 and 45° C. The purpose of the RNA digestion enzyme is to degrade non-hybridized probe that may be bound to the tube. It is important to remove the excess probe because secondary structures in the nucleic acid can be recognized by the detection means, resulting in elevated assay background. Preferably, the enzyme is added at a concentration between 0.05 and 0.5 mg/ml and is incubated for between 10 and 60 minutes. Most preferably, the enzyme is RNase A (Sigma, St. Louis, Mo.) and is incubated with the captured DNA for approximately 30 minutes at a concentration of 200 µg/ml. RNase III (NCI, Frederick, Md.) can also be used.

The RNase and conjugate are preferably diluted in a conjugation buffer that promotes specific antibody-antigen interaction, blocks non-specific binding of conjugate to the capture tube and stabilizes conjugate for long-term storage. A preferred buffer contains 0.1 M Tris™-HCl, pH 7.5, 0.6 M NaCl to reduce cross reaction of antibody with other nucleic acid species, $ZnCl_2$ and $MgCl_2$ for stabilizing alkaline phosphatase, normal goat serum to block non-specific interaction of conjugate with the capture surface, 0.25% of the detergent Tween™-20 to block non-specific binding of conjugate, and sodium azide as a preservative. A preferred wash buffer contains 0.1 M Tris™-HCl, pH 7.5, 0.6 M NaCl, 0.25% Tween™-20, and sodium azide as a preservative.

Detection of captured hybrid is preferably achieved by binding the above-described conjugated anti-hybrid molecule to the hybrid during this incubation. Tubes are then washed with the above-described wash buffer to remove any excess conjugate. Preferably, five manual washes are performed using either an Eppendorf™ Repeat Pipettor with a 50 ml Combitip™ pipette tip (Eppendorf, Hamburg, Germany), a Corning™ repeat syringe (Corning, Corning, N.Y.), a simple pump regulated by a variostat, or by gravity flow from a reservoir with attached tubing. Commercially available tube washing systems available from Source Scientific Systems (Garden Grove, Calif.) can also be used.

As described above, captured hybrid can also be detected with a direct labelled RNA probe, such as an enzyme-conjugated hybridization probe, or a hapten-modified probe that is subsequently detected by a labelled anti-hapten antibody.

Bound conjugate is subsequently detected by colorimetry or chemiluminescence as described by Coutlee, et al., *J. Clin. Microbiol.* 27:1002–1007 (1989). Preferably, bound alkaline phosphatase conjugate is detected by chemiluminescence with a reagent such as a Lumi-Phos™ 530 reagent (Lumigen, Detroit, Mich.) using a detector such as an E/Lumina™ luminometer (Source Scientific Systems, Inc., Garden Grove, Calif.) or an Optocomp I™ Luminometer (MGM Instruments, Hamden, Conn.).

Non-radioactive Hybridization Kit

The non-radioactive hybridization assay kit contains the necessary devices and reagents for performing the non-radioactive hybridization assay described above including an inert sample collection device, such as a dacron swab for exfoliated cell sample collection; sample transport medium for stabilization of the sample during transport to the laboratory for analysis; base, or hydrolysis reagent; one or more probes specific for the nucleic acid to be detected; neutralizing probe diluent; anti-hybrid antibody coated test tubes; a nuclease such as RNAase, preferably contained in a solution also containing a conjugated anti-hybrid antibody that can be detected by conventional means; and any necessary controls.

Preferably, the sample transport medium is the ViraPap™ Sample Transport Medium (STM) available from Digene Diagnostics, Inc. (Silver Spring, Md.); the base is 0.415 M NaOH; the neutralizing probe diluent is a BES/sodium acetate buffer; the test tubes are Ventrex Star™ tubes coated with a polyclonal anti-hybrid antibody; and the conjugated anti-hybrid antibody is a mouse monoclonal antibody conjugated to alkaline phosphatase. Preferably, the kit also contains a substrate for the chemiluminescent detection of alkaline phosphatase, such as a Lumi-Phos™ 530 reagent (Lumigen, Detroit, Mich.).

The kit should contain a negative control and a positive control for each probe. Preferably, the negative control is sonicated herring sperm DNA (100 pg/ml) dissolved in sample transport medium. The positive control preferably contains herring sperm DNA (100 pg/ml) and probe target nucleic acid.

In general, the assay can be used to detect as little as 1.0 pg to 10 ng DNA per ml of specimen with a typical specimen volume of 0.1 ml.

The following non-limiting examples illustrate use of the present assay and kit.

EXAMPLE 1

Detection of HPV in Clinical Human Cervical specimens

Cervical samples were collected with a dacron swab and stored in 1 ml ViraPap STM™ prior to analysis. All of the patients had a history of HPV infection. One-half ml (0.5 ml) of a 1.25 M NaOH hydrolysis reagent was added-to the 1 ml specimen for a final concentration of 0.415 N NaOH. The sample and swab were subjected to hydrolysis for 40 minutes at 65° C.

After hydrolysis, a 150 µl aliquot was removed from the sample tube and added to 50 µl of a probe diluent containing Probe A, B or C. Probe A contained RNA probes to HPV types 6, 11, 42, 43, and 44. Probe B contained RNA probes to HPV types 16, 18, 31, 33, 35, 45, 51, 52, and 56. Probe C contained RNA probes to HPV types 6, 11, 16, 18, 31, 33, and 35. Probes were synthesized from linearized plasmid template using phage T7 RNA polymerase. The probe diluent was a BES/sodium acetate buffer including 2 M BES, 1 M sodium acetate, 0.05% NaN$_3$, 5 mM EDTA, 0.4% of the detergent Tween-20 and 20% dextran sulfate. The pH of the probe diluent was between approximately 5 and 5.5. The probe mixture was hybridized at 65° C. for one hour.

Hybridized nucleic acids were captured onto an anti-hybrid coated Ventrex Star™ test tubes by shaking at 300–1000 rpm at room temperature for one hour. A solution containing RNAase at 0.2 mg/ml was added to digest any non-hybridized probe, and monoclonal anti-hybrid antibody conjugated to alkaline phosphatase was added to the captured hybrid. The excess RNase and conjugate was discarded, and tubes were washed five times with a buffer. Tubes were loaded into an E/Lumina™ luminometer for addition of LumiPhos™ 530 and measurement of chemiluminescence. The results are shown in Table I. The non-radioactive hybridization assay results were correlated with results using the ViraType™ HPV DNA test (Digene Diagnostics, Silver Spring, Md.) performed as described below. Three times background was used as the positive/negative cutoff in analysis of the data. The results with Probe C (6, 11, 16, 18, 31, 33, 35) correlated well with the ViraType™ results. One additional positive was detected with Probe C (patient 15) probably due to slightly better sensitivity of the non-radioactive hybridization assay. Additional positive patients (2, 9, 12 and 22) were identified with Probe A and Probe B, presumably due to the use of probes for additional HPV types.

The ViraType™ HPV DNA detection method is performed as follows. Exfoliated cervical cells are collected with a swab or scraper, or biopsies are obtained. The specimen is disrupted to release viral DNA, and the DNA is denatured and bound to a solid support by filtration through a set of three replicate nylon membranes having a high affinity for nucleic acids. HPV target DNA bound to the three replicate membranes is then hybridized to three $^{32}$P-radiolabelled RNA probe groups specific for HPV types 6/11, 16/18, or 31/33/35. Following hybridization, each of the three nylon membranes are treated with ribonuclease and washed to remove unhybridized probe. The presence of bound $^{32}$P-labelled RNA probe is detected by autoradiography of the three nylon membranes.

TABLE I

| Patient # | Probe A | Probe B | Probe C | ViraType | Comments |
|---|---|---|---|---|---|
| 1 | – | ++++ | ++++ | +++16/18 | |
| 2 | – | +++ | – | – | novel type, Probe B |
| 4 | – | – | – | – | |
| 5 | – | – | – | – | |
| 6 | – | – | – | – | |
| 7 | – | + | + | + 6/11, 16/18 | |
| 8 | – | – | – | – | |
| 9 | ++ | + | + | + 16/18 | suggests novel type, Probe A |
| 10 | – | – | – | – | |
| 11 | – | – | – | – | |
| 12 | – | ++++ | – | – | novel type, Probe B |
| 13 | – | + | + | ++ 16/18 | |
| 14 | – | – | – | – | |
| 15 | – | + | + | – | |
| 16 | – | + | + | ++ 16/18 | |
| 17 | – | + | + | ++ 16/18 | |
| 18 | + | +++ | +++ | ++ 16/18 | |
| 19 | – | – | – | – | |
| 20 | – | + | ++ | ++ 16/18 | |
| 21 | – | + | + | +/– 16/18 | |
| 22 | ++++ | – | + | +/– 16/18 | suggests novel type, |

TABLE I-continued

| Patient # | Probe A | Probe B | Probe C | ViraType | Comments |
|---|---|---|---|---|---|
| 23 | +++ | + | ++ | ++ 6/11, +/– 16/18 | Probe A |
| 24 | – | – | – | – | |
| 25 | – | ++++ | ++++ | ++++ 16/18 | |
| 26 | – | – | – | – | |
| 27 | – | +++ | +++ | +++ 16/18 | |
| 28 | – | – | – | – | |
| 29 | – | ++ | + | ++ 30's | |

EXAMPLE 2

Assay of Known Positive Samples

Samples known to be positive for HPV 16 infection based on results using the ViraType™ HPV detection kit (Digene Diagnostics, Silver Spring, Md.) were analyzed using the non-radioactive hybridization assay as described in Example 1 with an HPV 16-specific probe. The results indicated good correlation between the quantitative chemiluminescent assay and the semi-quantitative dot blot as shown in Table II.

TABLE II

Detection of Clinical Samples Using Antibody Tube Assay[1]: Correlation of ViraType Dot Blot Signal With Chemiluminescent Output

| Clinical Samples in order of ViraType Intensity | Chemiluminescent Output | ViraType Result |
|---|---|---|
| H215 | 453,986 | + |
| H216 | 506,927 | + |
| Y26 | 15,268 | + |
| H209 | 13,913 | + |
| Y25 | 17,745 | + |
| H409 | 12,168 | + |
| H357 | 5,451 | + |
| Y181 | 6,605 | + |
| H259 | 3,025 | + |
| Y205 | 3,219 | + |
| Y97 | 2,349 | + |
| H423 | 1,463 | + |
| Y44 | 2,048 | + |
| H347 | 1,107 | + |
| Y209 | 1,237 | + |
| H33 | 706 | – |
| Y110 | 628 | – |
| Y109 | 650 | – |
| H401 | 508 | – |
| Y98 | 785 | – |
| H297 | 487 | – |

Pool of 20 viraType Negative Samples

| 100 µl Assayed (no HPV added) | 10 pg HPV 16 DNA Added to 100 µl of negative pool |
|---|---|
| 458 | 1,386 |
| 429 | 1,366 |
| 447 | 1,496 |

[1]Tubes used in this assay were streptavidin coated tubes prebound with biotinylated polyclonal antibody.

EXAMPLE 3

Effect of Blood in Specimens

Interference by blood in specimens is one of the limitations of the HPV assays presently available. Blood does not interfere in the present non-radioactive hybridization assay.

cervical specimens were spiked with plasmid DNA and screened with the non-radioactive hybridization assay described in Example 1. The results are shown in Table III. Samples ranged from light to heavy blood contamination. Even in the bloodiest specimen, there was no interference in detection of target DNA, even though this sample contained brown particulate matter after hybridization.

TABLE III

Effect of Blood in specimens
Relative Light Units

| Sample | 10 pg HPV 16 DNA[1] | No DNA | Sample Description |
|--------|---------------------|--------|--------------------|
| A | 1014 | 40 | clean system |
| B | 1146 | 43 | clinical - clear |
| C | 1162 | 37 | clinical - pale yellow |
| D | 1000 | 37 | clinical - brownish yellow |
| E | 1221 | 40 | clinical - translucent brown |
| F | 1179 | 37 | clinical - dark rust |

[1]Average of duplicates.

EXAMPLE 4

Evaluation of Hybrid Capture HPV DNA Assay on a Panel of Clinically Characterized Specimens One-hundred and ninety-nine women with equivocal Pap smears were enrolled in a study. Each had a specimen of exfoliated cervical cells sampled by lavage and subjected to HPV DNA testing. The Pap smears of each woman were also re-read by a panel of expert pathologists who arrived at a consensus diagnosis. The specimens for HPV testing were placed in standard Sample Transport Medium manufactured by Digene Diagnostics, Inc. as part of its ViraPap™ test kit. Each specimen was tested with both the non-radioactive hybridization assay as set forth below and a Southern blot method well described in the literature and in particular by Lorincz A. T. et al., *J. Virol.* 58:225 (1986).

Samples were tested by the non-radioactive hybridization assay by first pipetting 500 μl hydrolysis reagent into control and sample tubes. The tubes were capped and vortexed and incubated in a 65° C. waterbath for 45±5 minutes. Appropriate mixtures of probes for oncogenic and non-oncogenic HPV were prepared as probes A and B respectively. A 50 μl aliquot of probe A, containing probes for HPV types HPV 6, HPV 11, HPV 42, HPV 43, HPV 44, was pipetted into hybridization tubes and 150 μl of denatured sample was added. A 50 μl aliquot of probe B containing probes for HPV types HPV 16, HPV 18, HPV 31, HPV 33, HPV 35, HPV 45, HPV 51, HPV 52, and HPV 56 was pipetted into a second set of hybridization tubes and 150 μl of denatured sample was added. Tubes were capped, vortexed, and incubated in a 65±2° C. waterbath for 60±5 minutes. The contents from each tube were transferred into corresponding capture tubes which had been coated with an anti-hybrid antibody and covered with Parafilm™. Tubes were shaken on a rotary shaker set at 1000 rpm at room temperature for 60±5 minutes. Tubes were decanted and blotted. A 250 μl aliquot of detection reagent containing an alkaline phosphatase-conjugated anti-hybrid monoclonal antibody and RNAase A was pipetted into each tube, shaken vigorously, and incubated at room temperature for 30±3 minutes. Tubes were decanted, washed five times, and drained. A 250 μl aliquot of a second detection reagent containing a chemiluminescent alkaline phosphatase substrate was pipetted into the tubes and incubated at room temperature for 30±3 minutes. Tubes were dried and read on a luminometer.

The data in Tables IV–VII show the performance of the non-radioactive hybridization assay versus clinical diagnoses (Tables IV–VI) and versus the reference standard Southern blot test (Tables VII and VIII). In Table IV, the numbers in parenthesis are the numerical values whereas the numbers not in parenthesis are percent values. In Tables V and VII, the non-radioactive hybridization assay contained RNA probes for the following HPV types: HPV 6, HPV 11, HPV 16, HPV 18, HPV 31, HPV 33, HPV 35, HPV 42, HPV 43, HPV 44, HPV 45, HPV 51, HPV 52, and HPV 56. In Tables VI and VIII, the non-radioactive hybridization assay contained RNA probes for the following high risk HPV types: HPV 16, HPV 18, HPV 31, HPV 33, HPV 35, HPV 45, HPV 51, HPV 52, and HPV 56.

The comparisons demonstrate that the non-radioactive hybridization assay for HPV DNA correlates well with the clinical diagnosis, and the values observed are similar to those reported in the literature using research methods. All these values are consistent with an accurate and useful HPV DNA diagnostic test. The correlation of the non-radioactive hybridization assay for HPV DNA to Southern blot shown in Tables VII and VIII also demonstrate a high level of accuracy for HPV DNA detection, especially when restricted to high risk HPV types.

TABLE IV

Prevalence of High Risk and Low risk
Human Papillomavirus Sets in 199 Women
with Atypical Pap Smears Reread by a
Panel of Pathologists.*

| HPV DNA Result by | Diagnostic Category Column Percent (Number) HPV DNA Positive | | | |
|---|---|---|---|---|
| Hybrid Capture | Normal | Equivocal | SIL+ | Total |
| Negative | 74 (89) | 42 (11) | 15 (8) | 54 (108) |
| Positive | 26 (32) | 58 (15) | 85 (44) | 46 (91) |
| High Risk | 17 (20) | 38 (40) | 77 (40) | 35 (70) |
| Low Risk | 10 (12) | 19 (5) | 8 (4) | 11 (21) |
| Total | (121) | (26) | (52) | (199) |

*Original diagnosis of all Pap smears was equivocal. Reclassification as shown in the table was the result of reread by 3 pathologists. + only 2 of 52 (4%) of SILs were high grade squamous intraepithelial lesions (HGSIL).

TABLE V

Contingency Table of HPV
Positive Versus SIL Using Hybrid Capture*

| | | SIL (clinical diagnosis) | | | Sens = 65 |
|---|---|---|---|---|---|
| | | + | − | | Spec = 74 |
| Hybrid | + | 44 | 32 | 76 | PPV = 58 |
| Capture | − | 8 | 89 | 97 | NPV = 92 |
| HPV | | 52 | 121 | 173 | Odds Ratio - 15 |

*Equivocals excluded.

TABLE VI

Contingency Table of High Risk
HPV Positive Versus SIL Using Hybrid Capture*

| | | SIL (clinical diagnosis) | | | Sens = 77 |
|---|---|---|---|---|---|
| | | + | − | | Spec = 83 |
| Hybrid | + | 40 | 20 | 60 | PPV = 67 |
| Capture | − | 12 | 101 | 113 | NPV = 89 |
| High | | 52 | 121 | 173 | Odds Ratio - 17 |

TABLE VI-continued

Contingency Table of High Risk
HPV Positive Versus SIL Using Hybrid Capture*

Risk
HPV

*Equivocals excluded.

TABLE VII

Evaluation of Hybrid Capture
Versus Southern Using the 199 Specimens
with Original Atypical Pap Smears
(the Schiffman Atypia Study)

|  |  | Southern Any HPV | | | |
|---|---|---|---|---|---|
|  |  | + | − | | |
| Hybrid | + | 75 | 16 | 91 | Sens = 81% |
| Capture | − | 14 | 94 | 108 | Spec = 85% |
| HPV |  | 89 | 110 | 199 | Accuracy = 85% |

Table VIII

|  |  | Southern High Risk HPVs | | | |
|---|---|---|---|---|---|
|  |  | + | − | | |
| Hybrid | + | 50 | 8 | 58 | Sens = 100% |
| Capture | − | 0 | 94 | 94 | Spec = 92% |
| High Risk HPV |  | 50 | 102 | 152 | Accuracy = 95% |

EXAMPLE 5

Evaluation of the Hybrid Capture HBV DNA Assay
in Specimens of Human Serum

Figure 2:
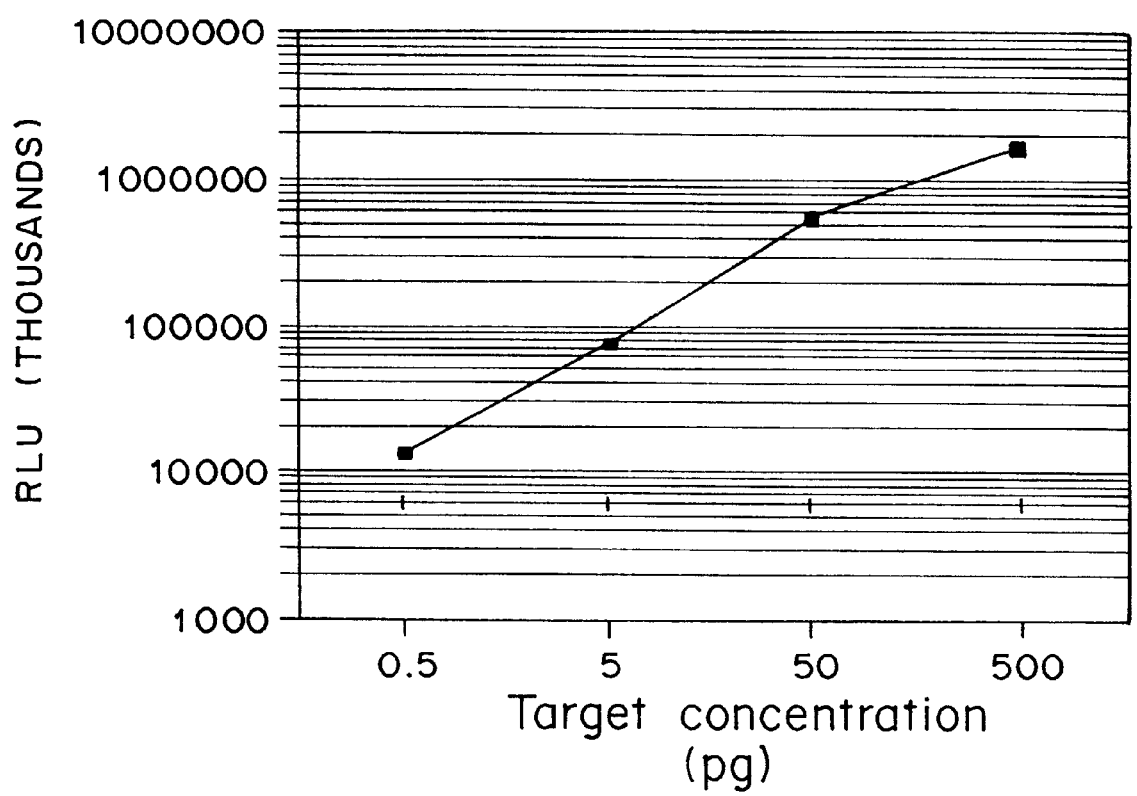
FIG. 2 is a logarithmic dose-response analysis of HBV DNA in human serum detected by the hybridization assay of the present invention showing a linear relationship between relative light units (RLU) and picograms of HBV DNA.

The non-radioactive hybridization assay was used to quantitate HBV DNA. Dose-response experiments were performed in clean model systems and also in human serum. The results of one such experiment are shown in FIG. 2. In this experiment various amounts of HBV target DNA were diluted into a negative specimen of human serum and then assayed by the method set forth below.

HBV DNA in serum samples was quantitated by the non-radioactive hybridization assay by pipetting 50 µl control or sample serum into test tubes. A 25 µl aliquot of ViraPap™ sample transport medium (Digene Diagnostics, Inc., Silver Spring, Md.) was pipetted into each tube. A 25 µl aliquot of protease was pipetted into each tube, and the tubes vortexed. Tubes were incubated in a 65±2° C. water bath for 20±5 minutes. A 50 µl aliquot of a hydrolyzing reagent was pipetted into each tube, and tubes were shaken to mix. A 50 µl aliquot of HBV probe was pipetted into each tube. Tubes were capped and vortexed, and incubated at 65° C. for 60±5 minutes. The contents of each tube were transferred to a capture tube coated with anti-hybrid antibody. The capture tubes were covered with Parafilm™ and shaken on a rotary shaker for 60 minutes. Tubes were decanted and blotted. A 250 µl aliquot of detection reagent containing RNAase A and an alkaline phosphatase-conjugated monoclonal antibody specific for the RNA/DNA hybrid was pipetted into each tube, tubes were shaken vigorously, incubated at room temperature for 30±3 minutes, decanted, washed five times and drained. A 250 µl aliquot of a second detection reagent containing a chemiluminescent alkaline phosphate substrate was pipetted into each tube and incubated at room temperature for 30±3 minutes. Tubes were dried and read on a luminometer.

These data, set forth in FIG. 2, show that the relationship between relative light units (RLUs) and picograms of DNA per 50 µl of assay volume is approximately linear between 0.5 pg and 500 pg.

In another experiment 84 specimens of human serum from different individuals were tested with the non-radioactive hybridization assay and with another well characterized dot blot test for HBV DNA known as the Hep-Probe™ test, commercially available from Digene Diagnostics, Inc. (Silver Spring, Md.). The results in Table IX demonstrate that the non-radioactive hybridization assay data were essentially equivalent, and slightly more sensitive, than the results obtained using the $^{32}$P-labelled RNA probe based dot blot system. Overall these results show that the non-radioactive hybridization assay for HBV DNA is an accurate, fast, and quantitative non-radioactive test for HBV DNA in human serum.

TABLE IX

Comparison of Hybrid Capture
HBV DNA Test to HepProbe ™

|  | Hep probe ™ | |
|---|---|---|
|  | + | − |
| HBV Hybrid + Capture − | 39 − | 2 43 |
|  | Sensitivity 100% | |
|  | Specificity 96% Accuracy = 98% | |

EXAMPLE 6

Evaluation of Hybrid Capture for the Detection of
*Chlamydia trachomatis* in Human Clinical
Specimens For this study Dr. Julius Schachter of the Chlamydia Laboratory, University of California, San Francisco, provided 54 cervical specimens which had been examined for chlamydia by direct culture. These specimens were not optimal for the non-radioactive hybridization assay described herein because they were not collected in the preferred sample transport medium. The specimens had been stored for several months prior to assay, and less than the preferred specimen volume of 100 µl was available in most cases. A preliminary analysis was performed with the non-radioactive hybridization assay as described in Example 4, except that the probe diluent contained a single probe specific for Chlamydia. The probe was the full length cryptic plasmid transcribed into RNA. Table X shows the results. The sensitivity of the DNA test was 79% and the specificity was 97%. The overall accuracy was 89% which is within an acceptable range.

TABLE X

Preliminary Results of Non-Radioactive Hybridization Assay Chlamydia vs. Schachter Chlanydia Culture

|  |  | Culture | | |
|---|---|---|---|---|
|  |  | + | − | |
| Hybrid | + | 19 | 1 | 20 |
| Capture | − | 5 | 29 | 34 |
|  |  | 24 | 30 | 54 |
|  |  |  | Sens = 79% | |
|  |  |  | Spec = 97% | |

Modifications and variations of the non-radioactive hybridization assay and kit will be obvious to those skilled in the art from the foregoing detailed description of the invention. Such modifications and variations are intended to come within the scope of the appended claims.

We claim:

1. A non-radioactive solution hybridization assay for the detection of a target nucleic acid sequence in a biological sample the improvement comprising the steps of:
   a) adding to the sample base to a final concentration of between 0.2 M and 0.8 M, at a temperature of between 60 and 70° C., for between 30 and 120 minutes, to hydrolyze the RNA in the sample and denature the target DNA;
   b) hybridizing the target DNA sequence in the treated sample to a complementary RNA probe to form a double-stranded DNA/RNA hybrid;
   c) capturing the hybrid onto a solid phase to which an anti-hybrid antibody or functional anti-hybrid antibody fragment has been immnobilized, wherein the antibody or antibody fragment specifically binds to a component of the double-stranded DNA/RNA hybrid;
   d) eliminating any non-hybridized probe by digestion with RNAse; and
   e) detecting the bound hybrid, wherein the detection of bound hybrid quantitatively indicates the presence of the target DNA sequence in the sample, wherein the assay provides an accuracy of at least about 89%.

2. The assay of claim 1 wherein the target DNA is selected from the group consisting of human papillomavirus DNA, hepatitis B DNA, and Chlamydia DNA.

3. The assay of claim 1 wherein the concentration of probe is between 1 and 500 ng/ml.

4. The assay of claim 1 wherein the concentration of probe is between 20 and 200 ng/ml.

5. The assay of claim 1 wherein the concentration of probe is approximately 75 ng/ml.

6. The assay of claim 1 wherein the base is sodium hydroxide in a concentration of between 0.415 M and 0.8 M, incubated with the sample at a temperature between 60 and 70° C. for a period of between 30 and 120 minutes.

7. The assay of claim 1 wherein the base is sodium hydroxide in a concentration of between 0.415 M and 0.8 M, incubated with the sample at a temperature between 60 and 70° C. for a period of between 30 and 60 minutes.

8. The assay of claim 1 wherein the base is sodium hydroxide in a concentration of approximately 0.415 M, incubated with the sample at a temperature of approximately 65° C. for a period of approximately 45 minutes.

9. The assay of claim 1 wherein the RNAase is added to the sample in a concentration between 0.01 and 1 mg/ml and incubated with the sample at a temperature between 4 and 45° C. for a period of between 5 minutes and 24 hours.

10. The assay of claim 1 wherein the RNAase is added to the sample in a concentration between 0.05 and 0.5 mg/ml and incubated with the sample at a temperature between 20 and 30° C. for a period of between 10 and 60 minutes.

11. The assay of claim 1 wherein the RNAase is added to the sample in a concentration of approximately 0.2 mg/ml and incubated with the sample at room temperature for a period of approximately 30 minutes.

12. The assay of claim 1 further comprising diluting the probe in a buffer that restores the sample to a neutral pH.

13. The assay of claim 11 wherein the buffer comprises 2-ethane sulfonic acid and sodium acetate.

14. A solution hybridization kit for the detection of a target DNA nucleic acid sequence for diagnosing genetic defects, microbial or viral infections in a biological sample with an accuracy of at least about 89%, the kit comprising:
   a) a sample transport medium for stabilization of the biological sample;
   b) a base solution having a concentration of base between 0.2 M and 0.8 M for hydrolyzing the RNA in the sample and denaturing the target DNA therein;
   c) an RNA probe complementary to the treated target DNA sequence for formation of a double-stranded DNA/RNA hybrid;
   d) a neutralizing probe diluent for diluting the probe and neutralizing the base;
   e) a solid phase to which an anti-hybrid antibody or an anti-hybrid antibody fragment has been immobilized, wherein the antibody is specific for a component of a hybrid formed by hybridization of the RNA probe and the target DNA sequence;
   f) RNAse for eliminating any non-hybridized probe; and,
   g) means for detecting the hybrid formed by hybridization of the probe and the target nucleic acid sequence.

15. The kit of claim 14 wherein the target nucleic acid is DNA selected from the group consisting of human papillomavirus DNA, hepatitis B virus DNA and Chlamydia DNA.

16. The kit of claim 14 wherein the base is sodium hydroxide in a concentration of between 0.415 M and 0.8 M.

17. The kit of claim 14 wherein the RNAse and detecting means are combined in a single reagent.

* * * * *